United States Patent [19]

Grunstein

[11] Patent Number: 5,261,397
[45] Date of Patent: Nov. 16, 1993

[54] METHODS AND APPARATUS FOR MEASURING INFANT LUNG FUNCTION AND PROVIDING RESPIRATORY SYSTEM THERAPY

[75] Inventor: Michael M. Grunstein, Merion, Pa.

[73] Assignee: The Children's Hospital of Philadelphia, Philadelphia, Pa.

[21] Appl. No.: 698,401

[22] Filed: May 10, 1991

[51] Int. Cl.$^5$ .............................. A61M 16/00
[52] U.S. Cl. ..................... 128/204.18; 128/204.23; 128/720
[58] Field of Search ............ 128/720, 725, 204.18, 128/204.21, 204.23

[56] References Cited

U.S. PATENT DOCUMENTS

| | | | |
|---|---|---|---|
| 3,410,264 | 11/1968 | Frederik | 128/720 |
| 4,031,885 | 6/1977 | Davis et al. | 128/720 |
| 4,036,222 | 7/1977 | Gillard et al. | 128/720 |
| 4,259,967 | 4/1981 | Vooren et al. | 128/720 |
| 4,671,297 | 6/1987 | Schulze, Jr. | 128/204.23 |
| 4,802,492 | 2/1989 | Grunstein | 128/720 |

OTHER PUBLICATIONS

Suratt, P. M., et al., "A pulse method of measuring respiratory system compliance," *J. Appl. Physiol.* 49(6):1116–1121 (1980).

Suratt, P. M., et al., "Lung compliance and its transient elevations measured with pulse-flow method," *J. Appl. Physiol.* 50(6):1318–1324 (1981).

Grunstein, M. M., et al., "Expiratory volume clamping: a new method to assess respiratory mechanics in sedated infants," *J. Appl. Physiol.* 62(5):2107–2114 (1987).

Kochi, T., et al., "Chest wall and respiratory system mechanics in cats: effects of flow and volume," *J. Appl. Physiol.* 64(6):2636–2646 (1988).

*Primary Examiner*—Edgar S. Burr
*Assistant Examiner*—Aaron J. Lewis
*Attorney, Agent, or Firm*—Woodcock Washburn Kurtz Mackiewicz & Norris

[57] ABSTRACT

Methods and apparatus for determining respiratory system compliance ($C_{rs}$) and resistance ($R_{rs}$) are disclosed. The present invention provides apparatus whereby an airflow is introduced to a patient via a set of one way valves such that the inspiratory and expiratory flow paths are separate. By selectively occluding expiration, $C_{rs}$ can be determined and, following subsequent release of the occlusion, the respiratory system time constant ($\tau_{rs}$) is measured, from which $R_{rs}$ can be derived. In another embodiment, by selectively occluding inspiration after expiration has been occluded, a drop in pressure due to the compliance of the lungs can be measured and from this and other data, another measure of $R_{rs}$ can be obtained. The introduction of an airflow into the patient permits the present invention to obtain passive and dynamic respiratory function data. Additionally, in certain embodiments, the present invention permits medication to be effectively introduced into the airways of the patient. The present invention also permits analysis of the airway pressure waveform to determine the relative homogeneity of the air passageways leading to the alveolar sacs.

22 Claims, 3 Drawing Sheets

METHODS AND APPARATUS FOR MEASURING INFANT LUNG FUNCTION AND PROVIDING RESPIRATORY SYSTEM THERAPY

The present invention relates to methods and apparatus for diagnosis and therapy of the pulmonary system. More specifically, the present invention relates to measuring the compliance of lung tissue, the resistance of small airways and to the introduction therapeutic agents into the lungs, particularly the lungs of an infant.

BACKGROUND OF THE INVENTION

Respiratory system compliance ($C_{rs}$) is a measure of the elastic properties of the lung and chest wall. One method of measuring $C_{rs}$ involves training conscious adults to relax their respiratory muscles to eliminate the perturbations they cause. However, it is difficult to achieve consistent results with such techniques due to the level of training required, and such training is impossible in infants. Respiratory system compliance can be measured in anesthetized subjects without concern for respiratory muscle contraction, but anesthesia lowers lung compliance and thus also lowers the overall respiratory system compliance. In the relaxation methods requiring training mentioned above, a subject inspires to a given volume, then relaxes against a closed mouthpiece while the pressure at the mouth and lung volume are recorded.

Another method of measuring respiratory system compliance employs externally applied pressures. A subject is observed while breathing normally and then either airway opening pressure is increased or body surface pressure is decreased, and the subject's breathing is again observed. Respiratory system compliance is calculated from the pressure change data and observed changes in the subject's lung volume. This latter method is described as a dynamic measure of compliance since the patient is breathing, while the above-described methods requiring training the patient to relax provide a static measure of compliance, since expiration results from the compliance of the lungs without the effects of chest muscle interaction.

Another technique for measuring static total respiratory system compliance is known as the pulse method. See Suratt et al., "A pulse method of measuring respiratory compliance," *J. Appl. Pysiol.* 49(b):1116-21 (1980). In the pulse method, a pulse airflow is introduced at the end of expiration, and the pressure at the mouth is measured during the pulse. By plotting volume vs. pressure, and calculating the slope of the resulting line, respiratory system compliance can be determined. In other words, compliance is calculated by dividing the airflow rate by the change in transrespiratory pressure. However, this method requires a subject be relaxed to some extent; in a unrelaxed subject, the pressure-volume plot will be non-linear. The pulse flow method is also useful for measuring static lung compliance ($C_L$). See, Suratt et al., "Lung compliance and its transient elevation," *J. Appl. Pysiol.*, 50(b):1318-24 (1981).

Static respiratory system compliance can also be determined while a subject is under sedation. See, Grunstein et al., "Expiratory volume clamping: a new method to assess respiratory mechanics in sedated infants," *J. Appl. Pysiol.* 62(5):217-14 (1987); U.S. Pat. No. 4,802,492—Grunstein incorporated herein by reference. In this method, the patient breathes through a two way valve such that expiration may be selectively blocked. When expiration is blocked, the inspiration flow path remains open, permitting the volume and airway pressure within the respiratory system to increase. However, in infants in particular, the Hering-Breuer reflex produces apnea at lung volumes above the resting end-expiratory level. The progressive recruitment of the Hering-Breuer reflex enables passive respiratory mechanics to be noninvasively determined over a wide range of lung volume. The expiratory volume clamping technique relies on expiratory occlusion accomplished by means of the two way valve system having separate inspiratory and expiratory ports described above. The expiratory valve is closed during normal breathing of a sedated patient and the volume, airflow and airway pressure are recorded. The occlusion is then suddenly released during an expiratory phase and the same data are recorded after release; these data are indicative of passive exhalation. As discussed by Grunstein et al., "Expiratory volume clamping: a new method to assess respiratory mechanics in sedated infants," *J. Appl. Pysiol.* 62(5):2107-14 (1987); and U.S. Pat. No. 4,802,492—Grunstein, referenced above, the determination of volume and pressure over an extended lung volume range permits the net respiratory system compliance to be determined. In addition, these same data permit the passive time constant ($\tau_{rs}$) to be derived from the slope of the volume vs. flow curve.

Although the methods disclosed by these references provide valuable and repeatable data, many of them provide information from a static state. Ideally, a passive and dynamic system would be provided to measure respiratory system compliance. Static methods produce no flow, while flow would occur in a dynamic system. Dynamic information is important since the effective stiffness of the lungs is influenced by the airways within the lung, e.g., the bronchi, bronchioles, and the resistance of these airways caused by the degree of narrowing therein. For example, when the airways are narrowed due to disease, e.g. asthma, emphysema and chronic bronchitis, the more rapidly breaths are taken the less the lungs expand. Currently, there is no readily applicable test of smaller airway function and their influence on the dynamic compliance of the lungs. Thus, it is an object of the present invention to measure the passive, dynamic mechanical properties of the respiratory system, particularly the respiratory systems of infants.

Moreover, it would be desirable to measure the passive time constant of the respiratory system and thus derive another measure of the resistance of the respiratory system. It is accordingly a further object of the present invention to provide methods and apparatus to collect and process such data.

Finally, in the case of infants, medicines such as bronchodilators used for treating conditions such as asthma are simply nebulized with the air in a breathing mask placed gently over the patient's face. However, droplets of medicine typically condense and collect in the mouth and throat region, never reaching the lungs, and in particular never reaching the smaller passageways within the lungs where the medicine will be the most efficacious. Therefore, it is yet another object of the present invention to provide methods and apparatus for effectively introducing a medicament into the lungs of a patient, particularly an infant.

SUMMARY OF THE INVENTION

These and other objects of the present invention are solved by providing a three way breathing apparatus in which a third branch is connected to a source of presurized air. By selectively positioning several one way valves, the flow can be regulated and by selectively occluding these valves data can be obtained that can be used to determine respiratory system compliance, pulmonary resistance and the respiratory system time constant. Additionally, the port through which the flow of pressurized air is introduced is preferably connected to a nebulizer through which a medicament can be introduced into the patient and, using the features of the present invention, can ensure that such medicament reaches the small airways in the lungs.

In a preferred embodiment, the present invention provides respiratory apparatus comprising a hollow body portion having an inlet and an outlet for permitting the passage of air therethrough. At least three one way valves are disposed within this body portion and at least two of these valves can be selectively occluded. A source of pressurized gas and a flow restrictor are connected to the body portion and an inlet is disposed between the first and the second one way valves. The flow restriction to which the source of pressurized gas is connected most preferably comprises a nebulizer and is connected to the body portion between the first one way valve and the second one way valve. A face mask is also provided for connecting the apparatus to the respiratory system of a patient. In use, both air flow and pressure are preferably sensed and a signal indicative of these values is generated. Preferably, the apparatus of the present invention also includes a safety valve for releasing pressure from within the body portion of the apparatus when the pressure exceeds a predetermined level. Most preferably, the above-described apparatus is adapted to be used with an infant patient.

The present invention also discloses methods for determining mechanical properties of a normally breathing patient comprising the steps of recording data indicative of the airway pressure, airflow and volume of the patient over time. The expiration of the patient is then occluded and the occlusion is then released. A change in volume and a change in pressure during the time interval prior to the release are determined and the change in volume is divided by the change in pressure, the resulting value representing the respiratory system compliance. Most preferably, the steps of determining the change in volume and pressure are undertaken during a time interval when these values are changing over time in a manner which is substantially linear.

The present invention also permits the respiratory system time constant to be determined by recording the relationship between volume and flow immediately following release of occlusion, and determining if the volume-flow relationship exhibits a substantially linear portion. In such a case, the slope of the substantially linear portion is determined and from that slope the respiratory time constant is determined.

The present invention also provides an alternative method by which the respiratory system resistance can be determined comprising the steps of occluding inspiration of the patient prior to releasing the expiratory occlusion. The airway opening pressure at a time prior to the advent of such inspiratory occlusion is measured and the immediate decrease in this pressure after inspiratory occlusion is also measured. Both the inspiratory and expiratory occlusions are then simultaneously released. By dividing the immediate decrease in pressure by the preceding constant flow value, determined between the time of expiratory occlusion and inspiratory occlusion, the respiratory system resistance can be determined.

DETAILED DESCRIPTION OF THE PREFERRED EMBODIMENTS

Figure 1:
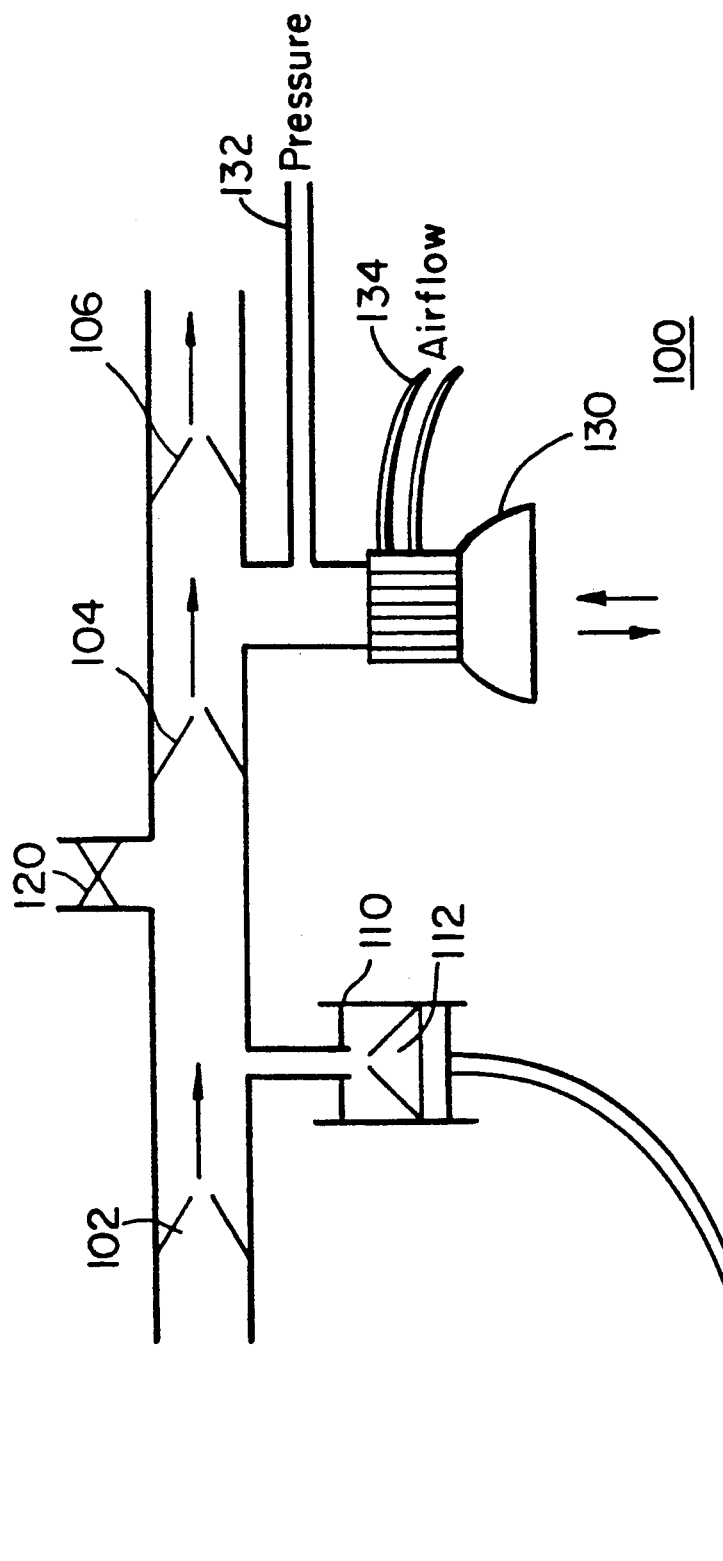
FIG. 1 is a partially schematic illustration of a preferred embodiment of the apparatus of the present invention.

Referring to FIG. 1, there is shown a preferred embodiment of a respiratory apparatus 100 made in accordance with the present invention. The apparatus 100 most preferably comprises a hollow tubular body portion and three one way valves 102,104,106 that control the flow of gases through the apparatus 100 as shown by the arrows. Thus, a first one way valve 102 permits air to flow into the body portion of the apparatus 100, from left to right as shown in FIG. 1. The second and third one way valves 104,106 are oriented to permit flow through the apparatus 100 and out to the atmosphere. A nebulizer 110 is preferably disposed between the first one-way valve 102 and the second one way valve 104. As known to those of ordinary skill in the art, the nebulizer 110 can create a spray of droplets that are carried into the respiratory apparatus 100 by an airflow 50. The airflow 50 may be from any of the typical sources available, such as a hospital air wall connection or the like. Most preferably, the nebulizer 110 also includes a one way valve 112. The restrictions created within the nebulizer 110 and the nebulizer valve 112 preferably reduce the pressure of the airflow 50 to an appropriate level. In certain embodiments of the present invention, the nebulizer 110 may be used without liquid and thereby functions only as a means for restricting flow. Alternatively, as explained in greater detail below, in certain embodiments, the nebulizer may admit water or medicament into the airflow 50 and thus into the patient.

A pressure relief valve 120 is preferably disposed between the nebulizer 110 and the second one way valve 104. At a predetermined pressure level, the pressure relief valve 120 automatically opens and permits the pressure to be reduced. The pressure relief valve 120 used in the present invention functions primarily as a safety device, however, as explained below, in certain embodiments the pressure relief valve 120 may be opened manually. The manual release of the pressure relief valve 120 causes the pressure to drop immediately to an intermediate, near steady state value, as further explained below. Since the flow path between the nebulizer 110 and the pressure relief valve is open, the pressure due to the respiratory system closes the second one way valve 104 creating an essentially closed system when expiration is occluded. The same effect can be accomplished using a pressure relief valve 120 that cannot be manually released by also providing a separate release valve (not shown) adjacent the pressure relief valve 120.

A face mask 130 for connecting the respiratory apparatus of the present invention to a patient is preferably disposed between the second one way valve 104 and the third one way valve 106. In a preferred embodiment of the apparatus of the present invention, a pressure sensor 132 and airflow sensor 134 are built into the face mask 130 preferably covering the nose and mouth. The design details of the face mask 130, as well as those of the pressure sensor 132 and airflow sensor 134 are well known to those of ordinary skill. In other embodiments, the mask 130 or other covering device may cover only the nasal passages or only the mouth or be replaced by a tracheal tube or other means of permitting air flow to enter the trachea and thus into the bronchia and lungs.

The considerations useful in selecting or designing the apparatus used in the present invention are set forth in Grunstein et al., "Expiratory volume clamping: a new method to assess respiratory mechanics in sedated infants," *J. Appl. Physiol.* 62(5):2107-14 (1987); U.S. Pat. No. 4,802,492—Grunstein, described above, which are both incorporated by reference as if fully set forth herein. The preferred flow rate for use in the present invention is the normal flow rate of infants, between 3.0 and 12.0 ml/sec/kg of body weight. The maximum pressure should not exceed 25 cm $H_2O$.

Upon inspiration through the face mask 130, airflow is pulled through the first one-way valve 102 and merged with the airflow 50 flowing through the nebulizer 110. The merged flow will pass through the second one way valve 104 and due to the lower pressure created by inspiration, will flow into the face mask 130. On the other hand, upon expiration, the second one way valve 104 will prevent the expired airflow from traveling in any direction except through the third one way valve 106.

In accordance witht the present invention, at least the first one way valve 102 and the third one way valve 106 may be selectively occluded. Expiration is thus preferably occluded by closing the third one way valve 106. An occlusion is created since, as explained above, the second one-way valve 104 prevents expired airflow from moving back through the apparatus 100. However, as explained in further detail below, the airflow 50 from the nebulizer/restriction 110,112 as well as the expiratory airflow can both enter the face mask 130, increasing the volume of the lungs and the pressure within the respiratory system upon each inspiration. In certain instances, explained below, the inspired flow of ambient air is also blocked when both inspiration and expiration are occluded. Inspiratory occlusion is preferably accomplished by closing the first one way valve 102. When both inspiration and expiration are blocked, airflow from all sources is cut off, and volume remains substantially constant. As explained below, a slight drop from maximum pressure is observed initially, with the pressure then remaining at a near constant value until both the inspiratory and expiratory occlusions are released.

Figure 2:
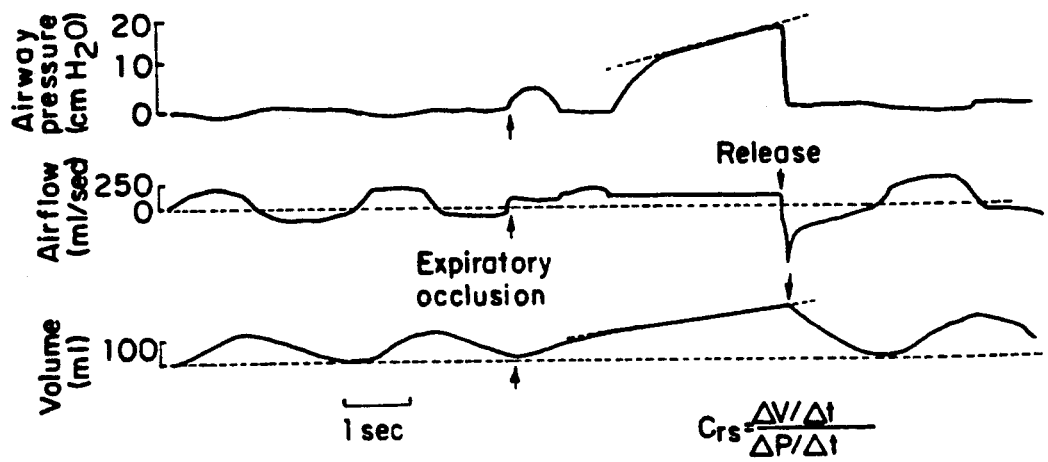
FIG. 2 graphically illustrates measurements of volume, airflow and airway pressure recorded using the present invention.

Referring now to FIG. 2, the operation of the present invention will be further explained by observing data collected from a patient. Although reference to FIG. 1 is helpful in this regard, it will be realized that numerous other types of apparatus other than that illustrated in FIG. 1 could perform the steps of the methods of the present invention FIG. 2 illustrates data indicative of the airway pressure, airflow and volume taken over time from a sedated patient. Initially, airway pressure is relatively constant and near atmospheric, and airflow and volume vary in a regular pattern. Expiratory occlusion is then produced, for example, by closing the third one way valve 106 shown in FIG. 1. After occlusion, pressure varies briefly and then begins to steadily rise; volume begins to rise immediately after expiratory occlusion. Airflow, however, no longer exhibits a rising and falling pattern with spontaneous respiration but instead assumes a steady state almost immediately after occlusion. The airflow does not fall to zero since the airflow 50 flowing through the nebulizer 110 continues to enter the patient. As shown in FIG. 2, at least a portion of those curves representing the rise in pressure and volume are substantially linear, during which time the patient is apneic due to the continuous activation of the Hering-Breuer reflex. The passive, dynamic compliance of the respiratory system can be derived by dividing the slope of the volume curve by the slope of the pressure curve, thus:

$$C_{rs} = \frac{\Delta V/\Delta t}{\Delta P/\Delta t}$$

Figure 4:
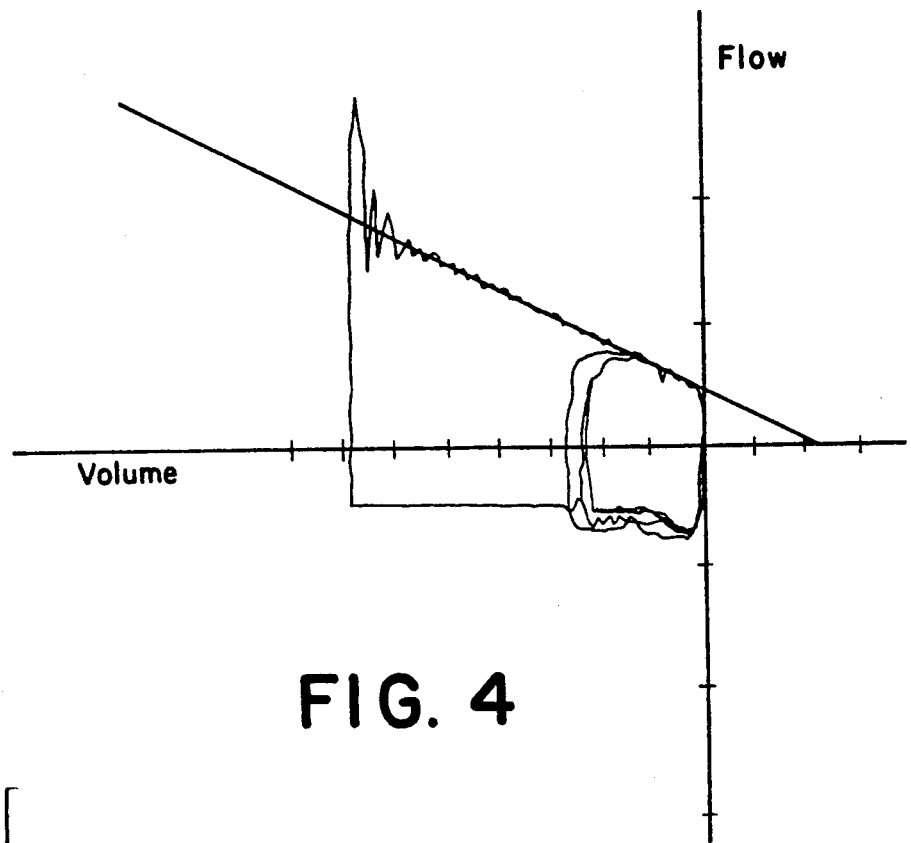
FIG. 4 depicts a plot of a volume-flow curve obtained using the present invention.

As explained above and illustrated in FIG. 4, these same data can be used to derive the time constant for the respiratory system, $\tau_{rs}$, by determining the slope of the volume-flow curve, obtained following release of the expiratory occlusion, which becomes substantially linear after initial oscillations due to inertia, thus:

$$\tau_{rs} = \frac{\Delta V}{\Delta \dot{V}}$$

and respiratory resistance can then be determined from the relation:

$$R_{rs} = \frac{\tau_{rs}}{C_{rs}}$$

The underpinnings of these formulae and their derivation in a static system is set forth in Grunstein et al., "Expiratory volume clamping: a new method to assess respiratory mechanics in sedated infants," *J. Appl. Physiol.* 62(5):2107-14 (1987); and U.S. Pat. No. 4,802,492—Grunstein, referenced above.

Figure 3:
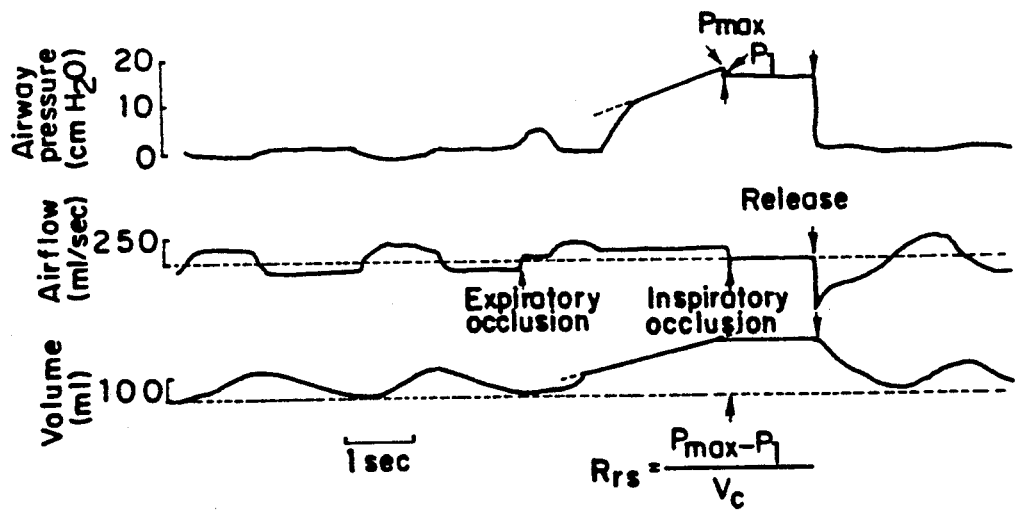
FIG. 3 is similar to FIG. 2 and illustrates data recorded using another embodiment of the present invention.

The present invention also permits an independent determination of respiratory system resistance in addition to that set forth immediately above. As seen in FIG. 3, and referring also to the apparatus of FIG. 1 for convenience, at a time after an expiratory occlusion that is sufficient to permit the rise in pressure and volume over time to be linear, an inspiratory occlusion is introduced. For example, in the apparatus illustrated in FIG. 1, inspiration can be occluded by closing the second one way valve 104. Referring again to FIG. 3, it can be seen that immediately after the inspiratory inclusion is introduced, flow drops to zero and volume remains at a steady state. However, pressure drops slightly from $P_{max}$ to a Pressure $P_1$, and then remains at a near steady state. It is known that the immediate drop in pressure after occlusion and its subsequent near plateau value permit the nonelastic and elastic properties of the respiratory system and its components to be derived. See Kochi, et al., "Chest wall and respiratory system mechanics in cats: effects of flow and volume," *J. Appl. Physiol.* 64(b):2636-46 (1988), which is incorporated herein by reference. Until the advent of the present invention, this phenomenon could only be observed in mechanically ventilated subjects by inflating the airways of a relaxed subject with a constant airflow. The present invention permits data to be collected from a normally breathing, sedated subject, e.g., presents a passive, dynamic system.

Using the present invention, the resistance of the respiratory system can therefore be determined by dividing the difference between the maximum pressure ($P_{max}$) and the pressure before inspiratory occlusion ($P_1$) by the constant flow ($\dot{V}_c$) obtained before inspiratory occlusion, thus:

$$R_{rs} = \frac{P_{max} - P_1}{\dot{V}_c}$$

Finally, in the embodiments of the present invention set forth and described above, the nebulizer 110 is preferably empty. However, it is possible to introduce a medicament into the nebulizer 110 that will be carried in the airstream 50 and through the face mask 130. When used in conjunction with an expiratory occlusion caused, for example by closing the third one way valve 106, the increased pressure of the system will aid in delivering the medicament into the lung tissue where it will be most efficacious.

Figure 5:
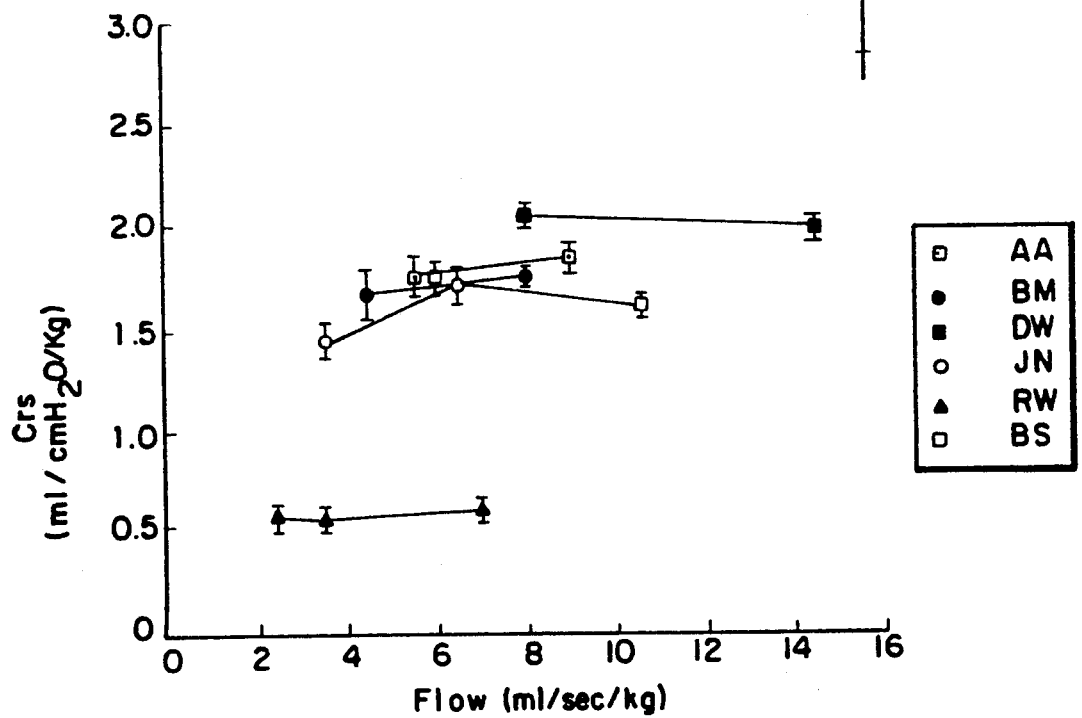
FIG. 5 is a plot that graphically depicts the correlation between the $C_r$° of several subjects measured at varying flow rates using the present invention.

Referring now to FIG. 5, there is illustrated a correlation plot illustrating the relative stability of the values of $C_{rs}$ measured using the present invention under varying flow rates. For the most part, the changes in flow have little effect on compliance when within a normal physiological range. Subject RN had stiff lungs, and therefore a low compliance due to interstitial lung disease. The present invention is thus flow independent in both normal patients and those with intrinsic parenchymal lung disease.

Referring again to FIGS. 3 and 4, it should also be noted that sometime after expiratory occlusion, the airway pressure rises for a period of time prior to attaining a substantially linear rate of increase. It has been determined that this non-linear rate of pressure change after expiratory occlusion is indicative of the homogeneity of the air passageways within the lungs. It is known that within the lung, different passageways exhibit different degrees of restriction. The overall level of homogeneity or inhomogeneity of these passageways are reflected in the rate at which pressure stabilizes after expiratory occlusion. Thus, in the ideal case, the non-linear portion of the pressure time curve would appear as a step function, rising immediately after expiratory occlusion.

It has now been found that the pressure waveform observed in a patient using the present invention can be analyzed and correlated to the respiratory system compliance. Preferably, the characteristic of the waveform is determined statistically by, for example, moment analysis. Using this technique it has been shown that the first moment of the mean pressure equilibration time correlates well with the respiratory system compliance determined using the present invention as explained above. Thus, it is possible to determine abnormalities within a patient since the pressure waveform observed may be compared to that of a "normal" patient. This conclusion is verified by the variance in respiratory system compliance of an "abnormal" patient measured using the present invention, as compared to that of a "normal" patient. The methods and apparatus of the present invention therefore permit analysis of the time course of pressure equilibration in the lungs to determine the homogeneity of the passageways leading to the alveolar sacs.

The respiratory apparatus described above, as well as the methods of the present invention, are particularly well suited for inclusion in a system for determining lung function. As well known to those of ordinary skill, the data collected by the present invention and the processing steps required can all be accomplished in an automated fashion, in real time and the results displayed, e.g., on a strip chart, oscilloscope, or cathode ray tube display. Graphical illustrations such as that shown in FIG. 5 can be generated to create empirical, qualitative knowledge helpful in diagnosing the condition of the patient. The present invention, therefore, in its broadest sense not only determines respiratory system resistance and compliance but instead presents a new clinical and diagnostic tool that permits infant lung function to be better understood.

Although the present invention has been described primarily in relation to problems associated with infants, those of ordinary skill will realize that the present invention is also useful in paralyzed adults. Additionally, the embodiments of the present invention set forth above are presented and are not meant to limit the scope of the present invention. Numerous adaptations, modifications and variations of the present invention are possible without departing from the spirit of the inventive concepts herein. Accordingly, reference should be made to the appended claims in order to determine the full scope of the present invention.

What is claimed is:

1. Respiratory apparatus comprising:
   a hollow body portion having an inlet and an outlet for permitting the passage of ambient air therethrough;
   at least three one way valves disposed within the body portion in spaced relation to one another, at least two of the valves being selectively occludable, wherein a first one way valve is disposed at the inlet, a third one way valve is disposed at the outlet, and a second one way valve disposed within the hollow body between the first and third one way valves;
   a source of pressurized gas connected to a flow restrictor connecting the pressurized gas to the body portion at a point between the first and second one way valves;
   a mask for connecting the apparatus to the respiratory system of a patient;
   an airflow sensor for generating a signal representing airflow; and
   a pressure sensor for generating a signal representing pressure.

2. The apparatus of claim 1, further comprising a safety valve for releasing pressure from within the body portion when the pressure exceeds a predetermined level.

3. The apparatus of claim 1, further comprising a means for generating a signal representing the volume of the airflow.

4. The apparatus of claim 1, further comprising a nebulizer connected to the flow restrictor.

5. The apparatus of claim 4, wherein the nebulizer is connected to the body portion at an inlet disposed between the first one way valve and the second one way valve.

6. The apparatus of claim 1, wherein the airflow sensor and the pressure sensor are disposed immediately adjacent the face mask, whereby the pressure and airflow in the region of the patient's mouth are measured.

7. The apparatus of claim 1, wherein the face mask is adapted to cover the mouth and nose of a patient.

8. The apparatus of claim 1, wherein the patient is an infant.

9. The apparatus of claim 4 wherein the nebulizer contains a medicament.

10. Respiratory apparatus comprising:
a hollow body portion having an inlet, an outlet and two selectively occludable one way valves and at least a third one way valve in a spaced-apart relationship, wherein a first one way valve is disposed at the inlet, a third one way valve is disposed at the outlet, and a second one way valve disposed within the hollow body between the first and third one way valves;
a source of pressurized gas flowing through a restrictor into the body portion;
means for connecting the body portion to a patient;
an airflow sensor; and
a pressure sensor.

11. The apparatus of claim 10 further comprising a nebulizer connected to the restrictor.

12. The apparatus of claim 10 wherein the means for connecting is a face mask.

13. The apparatus of claim 10 wherein the airflow and pressure sensors produce airflow and pressure signals respectively.

14. The apparatus of claim 13 further comprising means for displaying the airflow and pressure signals.

15. A method of determining the dynamic respiratory system compliance of a normally breathing patient comprising the steps of:
administering respiratory gas to the patient at a constant flow rate;
recording data indicative of the airway pressure, airflow and volume of the patient over time;
occluding the expiration of the patient while continuing to administer the respiratory gas at the constant flow rate;
releasing the expiratory occlusion while continuing to administer the respiratory gas at the constant flow rate;
determining the change in volume during a time interval prior to release;
determining the change in pressure during a time interval prior to release; and
dividing the change in volume by the change in pressure,
whereby dynamic respiratory system compliance is determined.

16. The method of claim 15, wherein the step of determining the change in volume is undertaken during a time interval of at least one second wherein the change in pressure over time is substantially linear.

17. The method of claim 15, wherein the step of determining the change in pressure is undertaken during a time interval of at least one second wherein the change in volume over time is substantially linear.

18. A method of determining the mechanical properties of the respiratory system of a normally breathing patient comprising the steps of:
administering respiratory gas to the patient at a constant flow rate;
recording data indicative of the airway pressure, airflow and volume of the patient over time;
occluding the expiration of the patient while continuing the administer the respiratory gas at the constant flow rate;
releasing the expiratory occlusion while continuing to administer the respiratory gas at the constant flow rate;
recording the relationship between volume and flow after release of expiratory occlusion;
determining the change in volume during a time interval prior to release;
determining the change in pressure during a time interval prior to release; and
dividing the change in volume by the change in pressure;
determining if the volume-flow relationship exhibits a substantially linear portion; and
determining the slope of the substantially linear portion,
whereby the respiratory system time constant is determined.

19. The method of claim 18, further comprising the step of inverting the respiratory system time constant, whereby the respiratory system resistance is determined.

20. A method of determining the mechanical properties of the respiratory system of a normally breathing patient comprising the steps of:
administering respiratory gas to the patient at a constant flow rate;
recording data indicative of the airway pressure, airflow and volume of the patient over time;
occluding the expiration of the patient while continuing to administer the respiratory gas at the constant flow rate;
occluding the inspiration of the patient prior to releasing the expiratory occlusion;
determining the maximum pressure at a time prior to the inspiratory occlusion;
determining the near steady state pressure of a time after the inspiratory occlusion;
releasing both the inspiratory and the expiratory occlusions while continuing to administer the respiratory gas at the constant flow rate;
determining the change in volume during a time interval prior to release;
determining the change in pressure during a time interval prior to release;
dividing the change in volume by the change in pressure; and
dividing the difference between the maximum pressure and the near steady state pressure immediately after inspiratory occlusion by the constant flow rate, whereby respiratory system resistance is determined.

21. The method of claim 16, further comprising the step of analyzing the change in pressure occurring during the time after the occlusion to expiration is introduced and before the change in pressure over time becomes substantially linear.

22. The method of claim 21 wherein the step of analyzing comprises determining the first moment of the mean pressure equilibration time.

* * * * *